(12) United States Patent
Sekino

(10) Patent No.: US 8,852,658 B2
(45) Date of Patent: Oct. 7, 2014

(54) ANTICANCER COMPOSITION

(75) Inventor: Yoshihiro Sekino, Fujisawa (JP)

(73) Assignee: Masahito Hoashi, Tokyo (JP)

( * ) Notice: Subject to any disclaimer, the term of this patent is extended or adjusted under 35 U.S.C. 154(b) by 0 days.

(21) Appl. No.: 13/466,918

(22) Filed: May 8, 2012

(65) Prior Publication Data

US 2012/0251644 A1    Oct. 4, 2012

Related U.S. Application Data

(62) Division of application No. 12/523,111, filed as application No. PCT/JP2008/001103 on Apr. 25, 2008, now abandoned.

(30) Foreign Application Priority Data

Nov. 15, 2007   (JP) ................. 2007-296553

(51) Int. Cl.
*A61K 36/00* (2006.01)
*A61K 36/18* (2006.01)
*A61K 36/185* (2006.01)

(52) U.S. Cl.
CPC .................... *A61K 36/18* (2013.01); *A61K 36/185* (2013.01)
USPC ............ 424/769; 424/725; 424/778; 424/774

(58) Field of Classification Search
None
See application file for complete search history.

(56) References Cited

U.S. PATENT DOCUMENTS

| | | | |
|---|---|---|---|
| 6,099,845 A | 8/2000 | Na et al. | |
| 6,132,725 A * | 10/2000 | Kadono et al. | ................. 424/769 |
| 6,267,993 B1 | 7/2001 | Kadono et al. | |

FOREIGN PATENT DOCUMENTS

| | | |
|---|---|---|
| JP | 11-130688 A | 5/1990 |
| JP | 2003-231641 | 8/2003 |
| KR | 2005003321 A | 1/2005 |
| WO | 2007-049846 | 5/2007 |

OTHER PUBLICATIONS

Kakiuchi et al, Inhibitory effect of tannins on reverse transcriptase from RNA tumor virus. Journal of Natural Products (1985) vol. 48, No. 4, pp. 614-621.*
Jin, U.-H. et al, "Induction of mitochondria-mediated apoptosis by methanol fraction of *Ulmus davidiana* Planch (Ulmaceae) in U87 glioblastoma cells", Environmental Toxicology and Pharmacology 22(2): 136-141 (2006).
Lee, J.-C. et al, "Plant-originated glycoprotein, G-120, inhibits the growth of MCF-7 cells and induces their apoptosis", Food and Chemical Toxicology 43(6): 961-968 (2005).
Lee, J.-C. "Flavonoid Fraction Purified from *Rhus verniciflua* Stokes Actively Inhibits Cell Growth Via Inducation of Apoptosis in Mouse Tumorigenic Hepatocytes", Natural Product Science 10(2): 74-79 (2004).
Yang, J. et al, "Chemical modification and antitumour activity of Chinese lacquer polysaccharide from lac tree *Rhus vernicifera*", Cabohydrate Polymers 59(1): 101-107 (2005).
Wang, D. et al, "Cytotoxic Effects of Mansonone E and F Isolated from *Ulmus pumila*", Biol. Pharm. Bull. 27(7): 1025-1030 (2004).
Pettit, G. et al., "Anti Neoplastic Agents Part 35 *Rhus trilobata*", Lloydia (Cincinnati), 37(3): 539-540 (1974).
Perchellet, et al., "Antitumor-Promoting Effects of Gallotannins, Ellagitannins, and Flavonoids in Mouse Skin in Vivo", ACS Symp Ser (Am Chem Soc), No. 546 pp. 303-327 (1994).
Supplementary European Search Report issued on Dec. 30, 2009, in corresponding European Patent Application No. 08751628.2.

* cited by examiner

*Primary Examiner* — Qiuwen Mi
(74) *Attorney, Agent, or Firm* — Browdy and Neimark, PLLC

(57) ABSTRACT

An anticancer composition containing a flowery portion of elm tree or its extract and a leaf portion of varnish tree or its extract is safe and shows high activity.

8 Claims, No Drawings

ANTICANCER COMPOSITION

TECHNICAL FIELD

This invention relates to an anticancer composition characterized by containing flowery portion of elm tree or its extract and a leaf portion of varnish tree or its extract.

BACKGROUND ART

Studies of developing pharmaceutical compositions by the use of the component derived from plants growing in the natural world have been heretofore actively made in the art. Of the plants existing in the natural world, those taken by animals and humans as edibles are nontoxic and readily available, and are therefore especially actively studied. Heretofore, various pharmaceutical compositions have been developed, and there are a great many kinds of those compositions.

Elm and vanish trees which the present inventors have specifically noted are plants abundantly growing in the natural world, and they are readily available. Heretofore, however, an elm tree has been almost put outside the range of studies for pharmaceutical materials. It is widely known that a vanish tree contains urushiol which is toxic and causes dermatitis when adhered to skin, and there is a strong impression that a vanish tree is harmful to human bodies. For these reasons, there have heretofore been few trials of utilizing elm and vanish trees for pharmaceutical materials as compared with other plants. In that situation, it has been found that a composition comprising elm and vanish trees selectively combined is useful for prevention or treatment for hypercholesterolemia, arteriosclerosis and liver dysfunction (see JP-A 2001-354581, 0045 to 0053).

SUMMARY OF THE INVENTION

However, the other physiological activities than the above of those plants have not been investigated at all, and the pharmaceutical applicability of the combined composition of elm and vanish trees is only extremely limited. Give that technical situation, the present inventors have promoted further assiduous studies of developing any additional novel pharmaceutical applicability of the combined composition of elm and vanish trees.

The present inventors have assiduously studied and, as a result, have found that a composition containing a component derived from a flowery portion of elm tree and a component derived from a leaf portion of varnish tree has excellent anticancer activities, whereby they have completed the invention.

That is, the present invention provides an anticancer composition containing a flowery portion of elm tree or its extract and a leaf portion of varnish tree or its extract. The elm tree used for the anticancer composition of the invention is preferably in *Ulmus hollandica*; more preferably selected from the group consisting of vegeta, commelin, groenveid, belgica, clusius, columella, dodoens and homestead; and particularly preferably selected from the group consisting of vegeta, commelin and groenveid. The anticancer composition of the invention may contain dried powder of the flowery portion of elm tree and dried powder of the leaf portion of varnish tree, or contain extract of the flowery portion of elm tree and extract of the leaf portion of varnish tree.

The present invention also provides an anticancer medicinal kit having at least two compositions characterized in that each of (1) a flowery portion of elm tree or its extract and (2) a leaf portion of vanish tree or its extract is contained in any one of the compositions constituting the kit.

The composition of the invention containing a flowery portion of elm tree or its extract and a leaf portion of varnish tree or its extract shows a strong anticancer activity. Since the composition of the invention shows low toxicity, it can be used as pharmaceuticals with a potent activity at a low dose, foods and beverages.

Description will now be made in detail of the anticancer composition of the invention. Although the following description of its structural features may often be made on the basis of typical embodiments of the present invention, it is to be understood that the present invention is not limited to any such embodiment. It is also to be noted that every numerical range as herein expressed by employing the words "from" and "to", or simply the word "to", or the symbol "-" is supposed to include the lower and upper limits thereof as defined by such words or symbol.

The anticancer composition of the invention contains a flowery portion of elm tree or its extract and a leaf portion of varnish tree or its extract.

Species of the elm tree used in the anticancer composition of the invention are not limited. The elm tree in *Ulmus hollandica* is preferably used in the invention. *Ulmus hollandica* includes crossed varieties between *Ulmus carpinifolla* and *Ulmus glabra* and often gives a relatively large appearance. Surface of the twig is smooth and bare no fruit at the center of the wing in general. *Ulmus hollandica* is planted popularly on roadsides and in parks in Europe, whose garden variety also known.

Plant species included in *Ulmus hollandica* are exemplified as elm tree such as vegeta, commelin, groenveid, belgica, clusius, columella, dodoens and homestead. Among them, vegeta, commelin, and groenveid are more preferable.

Vegeta is a very stout elm tree having a plurality of main branches. The main branches of the young tree tend to extend obliquely but they will usually become spread laterally and somewhat downward as they grow. Thus the most branches are rambling and scattered in all directions. The trunk has a lot of long cleft and appears as gray. Leaf of vegeta is larger than that of belgica, described later, and is more flat than that of commelin. The leaf is widened in its base and shaped in a variety of forms such as reverse-ovoid or oval. The bud is usually large and appears as glossy and reddish brown. Huntingdon elm tree is also classified as vegeta.

Commelin is a stout elm tree with an opened crown. The trunk usually climbs up by some spiral but straight upward as a whole. The branch is more sparse and thinner than that of vegeta, and the color is typically reddish brown. The crown can often be seen through from the ground. The leaf is light green and small, and the vein looks bright in general. The leaves are sparsely arranged and fall significantly later than those of vegeta. The leaf is typically shaped in oval and has a short and sharp tip. Commelin is wind-proof in general and defoliates late in the season.

Groenveid is a large and wind-proof elm tree. It is approx. 15 to 20 meters in height and the tree top is divided into several sections to exhibit slim and well-featured crown in general. The leaves are small, very densely arranged, colored in dark green and completely turns yellow in autumn. Rear surface of the leaf is covered with down and appears in some dark color. Since the plant is a slow grower capable of bearing relatively a large amount of flowers and fruits, it is beneficial in terms of obtaining a larger quantity of flowery portion required in the invention from a single plant of elm tree.

Clusius is a wind-proof elm tree with a well-featured crown. Columella is a small-bodied elm tree. Dodoens is a stout elm tree with glossy dark green leaves and upwardly climbing boughs. Homestead is an elm tree mainly cultivated in the United States. Dodoens and homestead have many resemblances to vegeta.

*Ulmus hollandica* used in the invention includes crossed varieties between *Ulmus carpinifolla* and *Ulmus glabra*.

*Ulmus carpinifolla* is approx. 25 to 30 meters in height and has a widened oval tree form. The wood texture becomes rougher with age. The twig is relatively thin and typically has no hair. In some species, phelloderm may be obviously formed on protogenic young branches. The leaf is shaped in reverse-ovoid, has a length of less than 8 cm in general, and has approx. 12 pairs of veins extended toward right and left.

*Ulmus carpinifolla* includes a wide variety of elm trees such as Dampieri, Hoersholmiensis, Sarniensis and Wredei.

*Ulmus glabra* on the other hand is a large elm tree with a widened and round crown. The root is less developed. The bark, colored in gray, is smooth in its early days and is then shallowly grooved. Thick brown boughs are densely arranged and bark of the crown is colored in pink. The leaf is 8 to 16 cm long and the texture of which is often rougher than that of *Ulmus carpinifolla*. The petiole is generally short, entire part of which is overlapped with the slant leaf base. The veins extending toward right and left are composing 12 to 18 pairs. The inflorescence is rather large. The wing for flying the seed has a reverse-ovoid shape and bears the fruit in its center.

Elm trees included in *Ulmus glabra* are, for example, Camperdownii, Exoniensis and Horizontalis.

It is allowable in the invention to use any plant species or elm trees other than those mentioned above.

It is also allowable in the invention to use any plant species obtained by crossing a plant species in *Ulmus hollandica* or other elm trees with other plant species. Other plant species to be crossed with may be one of the other elm trees or one of the trees other than elm trees. Either one or more kinds of species may be crossed. A crossed species may further be crossed. Thus the anticancer composition of the invention includes all of those obtained from any plant species originated from elm trees, such as in *Ulmus hollandica*.

These elm trees may be used separately or in combination with others in the invention.

The invention utilizes the flowery portion of elm trees. The plant species in *Ulmus hollandica*, for example, typically bears bud in the season from winter to early spring and blooms in spring. The flower bud may be small in size. It is thus desirable to collect the flowery portion within a period from its bud stage to the flower fall.

The flowery portion of the elm trees is utilized in any form convenient for use as an anticancer composition. It is allowable, for example, to use a mixture of finely stripped or powdered flowery portion as mixed with appropriate components, or to use an extract obtained by extraction using a proper solvent.

Fine stripping or powdering of the flowery portion is enabled by processing the collected flowery portion using a cutter, a stripper or a colloidal mill and is more favorably done after the flowery portion is dried. The flowery portion is usually dried until the moisture content drops below 10 wt %, preferably below 5 wt % and still more preferably below 3 wt %. Either natural drying or mechanical drying is allowable. The drying is preferably started within 30 minutes after the collection of the flowery portion.

There is no special limitation on drying temperature. Thus drying by rapid heating is possible using a pressure drum heater or electromagnetic wave. Drying using the pressure drum heater is preferably done within a range from 80 to 140° C. A drying period is usually set within two minutes, more preferably within one minute, and still more preferably within 40 to 50 seconds. Electromagnetic wave-aided drying using a microwave oven is possible, for example, at 600 W for 20 to 50 seconds. Heating and drying under such conditions can suppress or inactivate undesirable activities of enzymes contained in the flowery raw material and can prevent to a certain extent physiologically active substances from being degraded.

The flowery portion dried by the rapid heating may be used as it is or after dried further at low temperatures. The low temperature drying is preferably effected within a range from −5 to 10° C., which is effected by using a hot wind dryer such as an infrared dryer, ventilating heater or chilled dryer in a separate or combined manner. A possible case relates to, for example, infrared drying followed by chilled drying. Such low temperature drying can prevent physiologically active substances from being degraded.

The stripping or powdering of the flowery portion is effected using devices or tools selected by purposes. A colloidal mill, for example, can yield powder with a grain size of 50 to 100 μm. Such stripping or powdering is done before the drying, after the high temperature drying or after the low temperature drying.

Besides being processed into such strip or powder, the flowery portion is possibly used also as an extract. The flowery portion to be extracted is any one of collected flowery portion itself, strip of the collected flowery portion, and those after being dried at high or low temperatures. It is preferable to make the flowery portion into strips to a certain fineness to raise extraction efficiency. Favorable solvents for the extraction include water and alcohols, whereas other extraction solvents also allowable. The alcoholic solvents are typically referred as to methanol, ethanol, propanol, isopropanol, butanol, isobutanol, tert-butanol, pentanol, isopentanol, hexanol and isohexanol. These solvents are used separately or in combination with the other. For example, a 30 to 50% ethanol aqueous solution or methanol aqueous solution is applicable.

The extraction is possibly performed at the room temperature or under reflux. An extraction device such as Soxhlet extractor is also available. A typical method relates to an extraction using a 50% ethanol aqueous solution under the reflux temperature in a Soxhlet extractor for 30 to 60 minutes.

Although obtained extract is available per se as an anticancer composition, it is more preferable to use it after concentration aiming at a higher effect. Degree of the concentration differs according to use environments. The solvent may be removed from the extract to obtain powder. The powder may be dissolved in other solvent such as physiological saline for adjusting the concentration of the anticancer composition of the invention. In the case where the anticancer composition of the invention is used in solution, solid content of the solution is preferably 1 to 20% by weight, more preferably 2 to 15% by weight, further more preferably 3 to 13% by weight, still further more preferably 5 to 10% by weight.

In the anticancer composition of the invention, a leaf portion of varnish tree or its extract is used with the flowery portion of elm tree or its extract.

Varnish trees to be used are chosen from Anacardiaceae. A most preferable source relates to leaf portion of plant species in *Rhus* of Anacardiaceae. Such species include *Rhus vernicitlua, Rhus trichocarpa, Rhus ambigna, Rhus javanica* and *Rhus sylvestris*. Soft young leaves are preferable as the leaf portion of these varnish trees. The leaves of eight-week-old or younger are more preferable, and those of four-week-old or younger are sill more preferable.

The leaf portion of these varnish trees may be dried, powdered, stripped or extracted according to the above-mentioned processes similarly to those for the flowery portion of elm trees. Mixing ratio of the flower-derived component of elm trees and the leaf-derived component of varnish trees can be determined appropriately. It is generally set in a range of 1:0.1 to 10, preferably in a range of 1:0.3 to 3, and more preferably in a range of 1:0.5 to 2.

The composition of the invention that comprises a flowery portion of elm tree or its extract, and a leaf portion of vanish tree or its extract has an anticancer effect. Accordingly, a preventively or therapeutically effective amount of the anticancer composition of the invention may be dosed to mammals including humans for prevention or treatment for cancer. "Prevention" as referred to herein is meant to indicate a concept including prevention of cancer onset, metastasis and implantation; and "treatment" as referred to herein is meant to indicate a concept that includes repression of cancer development such as cancer cell growth repression and cancer reduction, and includes relieving of cancer signs and symptoms.

Specific examples of the cancer to which the anticancer composition of the invention is applied include malignant lymphoma, malignant melanoma, esophageal cancer, gastric cancer, large bowel cancer, rectal cancer, colon cancer, ureteral tumor, lung cancer, gallbladder cancer, bile duct cancer, biliary tract cancer, breast cancer, liver cancer, pancreatic cancer, testicular tumor, maxillary cancer, tongue cancer, lip cancer, oral cancer, pharyngeal cancer, laryngeal cancer, ovarian cancer, uterine cancer, prostate cancer, thyroid cancer, brain tumor, Kaposi sarcoma, angioma, leukemia, polycythemia vera, neuroblastoma, retinoblastoma, myeloma, bladder tumor, sarcoma, osteosarcoma, myosarcoma, skin cancer, basal cell cancer, skin appendage carcinoma, skin metastatic cancer, cutaneous melanoma, mesenchymal tumor, soft tissue sarcoma, etc., to which, however, the anticancer composition of the invention is not limited. In particular, the anticancer composition of the invention is especially effective for malignant sarcoma, malignant adenoma, hemangiosarcoma, non-Hodgkin lymphoma, mesenchymal tumor and soft tissue sarcoma.

The anticancer composition of the invention is applicable in a variety of styles by purposes.

For the case that an anticancer composition of the invention is used as pharmaceuticals, various medicine forms are selectable according to the dosal route. The anticancer composition of the invention is dosed either orally or parenterally, where typical doses include intrarectal dose, intranasal dose, buccal dose, hypoglossal dose, transvaginal dose, intramuscular dose, hypodermic dose and intravenous dose. Among them, oral dose, hypodermic dose and percutaneous doses are preferable, and oral doses are more preferable.

Formulations suitable for the oral dose include tablet, capsule, powder, subtilized granule, granule, solution and syrup; and those suitable for the parenteral dose include injection, intravenous drip, suppository, inhalant, percutaneous absorbent, transmucosal adsorbent and cataplasm. The injection can be any one of those used in intravenous injection, intramuscular injection, hypodermic injection and intravenous drip. The anticancer composition of the invention most preferably has a form of oral formulation, injection or cataplasm.

The anticancer composition of the invention may be added with, as required, additives allowable in terms of pharmacology and medicine production. Possible additives include, for example, vehicle, disintegrator, disintegrator adjuvant, binder, lubricant, coating agent, dye, diluent, base, solubilizing agent or solubilizing adjuvant, isonicity, pH adjuster, stabilizer, propellant, adhesive, and moistening agent. The anticancer composition of the invention may be added with the other physiologically active substances (for example, moutan cortex, polygonati Rhizoma, *Daucus carota* L., *Litchi chinensis* and *Licium barbarum*). Proper combination of these additives can provide various additional functions to the anticancer composition of the invention.

Specific examples of the vehicle include starch, cornstarch, white sugar, lactose, mannitol, carboxymethyl cellulose, inorganic salts, etc.

Specific examples of the disintegrator or the disintegrator adjuvant include wheat starch, rice starch, corn starch, potato starch, partially-alphatized starch, hydroxypropyl starch, carboxymethyl starch sodium, tragacanth, crystalline cellulose, methyl cellulose, low-substitution hydroxypropyl cellulose, carmellose, carmellose calcium, carmellose sodium, croscarmellose sodium, etc.

Specific examples of the binder include agar, gelatin, wheat starch, rice starch, corn starch, potato starch, dextrin, alphatized starch, partially-alphatized starch, hydroxypropyl starch, crystalline cellulose, crystalline cellulose/carmellose sodium, methyl cellulose, hydroxypropyl cellulose, low-substitution hydroxypropyl cellulose, hydroxypropylmethyl cellulose, hydroxypropylmethyl cellulose phthalate, hydroxypropylmethyl cellulose acetate succinate, carmellose sodium, ethyl cellulose, carboxymethylethyl cellulose, hydroxyethyl cellulose, pullulan, polyvinylpyrrolidone, aminoalkyl methacrylate copolymer, methacrylic acid copolymer, polyvinyl acetal diethylaminoacetate, polyvinyl alcohol, gum arabic, powder of gum arabic, white shellac, tragacanth, purified white sugar, macrogol, etc.

Specific examples of the lubricant include wheat starch, rice starch, corn starch, sucrose fatty acid ester, stearic acid, calcium stearate, magnesium stearate, hydrous silicon dioxide, light silicic anhydride, hydrous aluminium silicate, dry aluminium hydroxide gel, talc, magnesium metasilicate aluminate, calcium hydrogenphosphate, anhydrous calcium hydrogenphosphate, wax, hydrogenated oil, polyethylene glycol, etc.

Specific examples of the surfactant include sucrose fatty acid ester, soybean lecithin, polyoxyl stearate, polyoxyethylene-hardened castor oil, polyoxyethylene polyoxypropylene glycol, sorbitan sesquioleate, sorbitan trioleate, sorbitan monostearate, glycerin monostearate, sorbitan monopalmitate, sorbitan monolaurate, polysorbate, sodium laurylsulfate, lauromacrogol, etc.

In the anticancer composition of the invention, it is possible to design the anticancer composition so that the active component is released gradually as required. It is also possible to design the anticancer composition so that the active component is released in a concentrated manner at internal body sites where the component is needed. Such controlled release formulation or drug delivery system is prepared according to processes generally known in the pharmaceutical industry.

Organic or inorganic carrier is applicable to the anticancer composition of the invention. Such carrier includes lactose, starch, or oils and fats from plants or animals. An active component originated from flowery portion of elm tree and leaf portion of varnish tree is available within a range of 0.01 to 100% to the anticancer composition of the invention.

When the composition of the invention is administered, the component derived from a flowery portion of elm tree and the component derived from a leaf portion of varnish tree may be administered simultaneously or nonsimultaneously. For example, first the component derived from a flowery portion of elm tree may be administered and then the component derived from a leaf portion of varnish tree may be administered, and vis versa. The simultaneous administration of these components is preferable. The anticancer composition of the invention may be those where each of the component derived from a flowery portion of elm tree and the component derived from a leaf portion of varnish tree is contained in a separate container and they are mixed when use. The invention thus includes an anticancer medicinal kit having at least two composition in which each of (1) a flowery portion of elm tree or its extract and (2) a leaf portion of vanish tree or its extract is contained in any one of the compositions constituting the kit.

It is acceptable that the components (1) and (2) are contained in any one of compositions constituting the anticancer medicinal kit. The kit may be, for instance, such that comprising a composition containing component (1) and a composition containing component (2), or that comprising a plurality of compositions individually containing components (1) and (2) at different ratios. At the time of their use, these compositions can be directly dosed or can be properly combined and dosed.

The anticancer composition of the invention may dose to the humans and the mammals except humans (e.g. dogs). Dose of the anticancer composition of the invention is determined according to various conditions such as therapeutic or preventive purposes, sexuality, weight and age of patients, types and degrees of disease, medicine form, dosing route and number of times of dosing. Typical oral dose is effected with a dose of 0.1 μg to 100 mg (dry weight of active components)/kg weight/day and is given once a day or divided into several times, where the dose is not limited in the above range.

The anticancer composition of the invention may not be limited to that having a pharmaceutical form. The anticancer composition of the invention may be contained, for example, in various foods or beverages to provide safe and effective functional foods or functional beverages. The anticancer composition of the invention may be used in foods and beverages labeled as they have an anticancer activity. It may be added, for example, to black tea, refreshing drink, juice, candy, starchy foods and various processed foods, but examples are not limited to those. Amount of the active component originated from a flowery portion of elm tree and a leaf portion of varnish tree is selected within a range from 0.1 to 99% by weight. It is also possible to use gelling agent or so as required to improve pleasantness to the palate.

The invention will be detailed hereinafter referring to the several preferred embodiments. Components, ratios and procedures shown in these embodiments can properly be altered without departing from the spirit of the invention. Thus the scope of the invention is not limited to the following embodiments.

Example 1

An example of the anticancer composition of the invention (solution) will be described.

Flower buds of vegeta, commelin and groenveid, all of which belong to *Ulmus hollandica*, were collected in March in Amsterdam City, the Netherlands. The collected flower buds were respectively crushed with a mixer and dried at 110 to 120° C. until the moisture contents were reduced to 1 to 5%. The obtained dried powders were sealed with a deoxidizing agent and stored at room temperature.

Young leaves of a varnish tree were collected in March in Ishikawa Prefecture, Japan, crushed with a mixer, and dried at 110 to 120° C. until the moisture contents were reduced to 1 to 5%. The obtained dried powder was sealed with a deoxidizing agent and stored at room temperature.

After storage for a week, 7.5 g of the dry powder of elm tree and 7.5 g of dry powder of varnish tree were mixed together. Added was 100 ml of 70% ethanol to the powder mixture and the resultant was agitated for five hours to concentrate to the solid content of 58% by weight. The concentrated mixture was dissolved in a saline water to obtain solution samples of the invention having the concentration of 5%, 10%, 15% and 20%.

Example 2

An example of the anticancer composition of the invention (powder) will be described.

The dried powder of flowery portion of elm tree and a young varnish tree leaves prepared in Example 1 and starch were mixed according to the table below. Thus mixed powder having anticancer activities was prepared.

TABLE 1

| Components | Weight part |
| --- | --- |
| Dried powder of flowery portion of elm tree | 5 |
| Dried powder of young varnish tree leaves | 10 |
| Starch | 85 |

Example 3

A typical example of an anticancer composition (capsule) of the invention will be described.

The powder formulations prepared in Example 1 were filled in gelatin capsules to prepare capsule formulations having anticancer activities.

Example 4

A typical example of an anticancer composition (injection) of the invention will be described.

A mixture was obtained by mixing 7.5 g of the dried powder of flowery portion of elm tree and 7.5 g of the dried powder of young varnish tree leaves each prepared in Example 1. The mixed dried powders were extracted with water at 80° C. and the solvent was then removed under reduced pressure. The obtained extracts were dissolved with sodium chloride into distilled water. The extracts, sodium chloride and distilled water were mixed according to the quantities given in the table below. The resultant aqueous solutions were filtered to produce injections having anticancer activities.

TABLE 2

| Components | Weight part |
| --- | --- |
| Extract | 0.5 |
| Sodium Chloride | 1.5 |
| Distilled water | 98.0 |

Example 5

Typical examples of functional beverage of the invention having anticancer activities will be described.

A mixture was obtained by mixing 7.5 g of the dried powder of flowery portion of elm tree and 7.5 g of the dried powder of young varnish tree leaves each prepared in Example 1. The mixed dried powders were extracted with water at 60° C. The obtained extracts were concentrated to a solid content of 10% and then mixed with the components to obtain the composition shown in the table below. Functional beverages having anticancer activities were thus prepared.

TABLE 3

| Components | Weight part |
| --- | --- |
| Extract | 5.0 |
| Fructose glucose liquid sugar | 11.0 |
| Citric acid | 0.2 |
| Sodium citrate | 0.1 |
| Apple juice | 3.0 |
| Apple flavor | 0.2 |
| Water | 80.5 |

Test Example 1

In this Test Example, the anticancer compositions obtained in Example 1 were tested for the anticancer effect thereof.

A liquid preparation prepared Example 1, having a concentration of 10%, was orally administered to three adult dogs (body weight, 45±5 kg; 5 to 6 years old; Great Dane, etc.) all having hemangiosarcoma, at a dose of 1.5 ml, twice a day continuously for 50 days; thereafter the same liquid preparation but having a concentration of 15% was administered thereto for 15 days and then the same liquid preparation but having a concentration of 20% was administered thereto for 30 days. 30 days, 65 days and 95 days after the start of the administration, the dogs were analyzed for the size of the hemangiosarcoma thereof and for the presence or absence of metastasis therein. The results are shown in Table 4 below. The adult dog 1 died of an infectious disease, and its data after 60 days were not collected.

TABLE 4

| | Adult dog 1 | | Adult dog 2 | | Adult dog 3 | |
| --- | --- | --- | --- | --- | --- | --- |
| | Size of sarcoma (cm) | Metastasis | Size of sarcoma (cm) | Metastasis | Size of sarcoma (cm) | Metastasis |
| Start | 1.9 | — | 0.8 | — | 0.6 | — |
| After 30 days | 0.6 | Nothing | 0.2 | Nothing | 0.3 | Nothing |
| After 65 days | — | — | 0.2 | Nothing | 0.2 | Nothing |
| After 95 days | — | — | 0.2 | Nothing | 0.2 | Nothing |

After 95 days from the start of the administration, the liquid preparation having a concentration of 15% was kept administered to the adult dog 2 and the adult dog 3, but no change was found in them. During the term of the administration, the dogs showed no side-effects such as vomiting, diarrhea, decreased appetite and the like, and their renal function and liver function were kept on a normal level and their body weight increased.

In the same test, the liquid preparation of Example 1 was administered along with an antibiotic and an analgesic, in which, however, the liquid preparation of Example 1 did not interfere with the effect of the side-by-side therapeutical agents, antibiotic and analgesic. In addition, the side-by-side therapeutical agents did not interfere with the anticancer effect.

On the other hand, in the dogs of the control group to which the liquid preparation of Example 1 was not administered, the hemangiosarcoma subcutaneously grew and rapidly spread by metastasis, and the dogs died in 6 to 8 weeks.

Test Example 2

Also in this Test Example, the liquid preparation obtained in Example 1 was tested for the anticancer effect thereof.

With orally administering the liquid preparation obtained in Example 1, having a concentration of 10%, to an adult dog 11 (body weight, 50±5 kg; 6 to 7 years old; Great Dane) having hemangiosarcoma, at a dose of 3 ml, twice a day continuously for 33 days, the dog was given a blood test. Typical data of the test result are shown in Table 5 below.

TABLE 5

| | Adult dog 11 | | | | |
| --- | --- | --- | --- | --- | --- |
| | Creatine (mg/ml) | SGOT/ASAT (U/L) | SGPT/ALAT (U/L) | LDH-L (U/L) | Alkaline phosphatase (U/L) |
| Start | 13 | 55 | 51 | 338 | 89 |
| After 33 days | 13.9 | 45 | 45 | 118 | 79 |
| Standard | 5~15 | 16~43 | 15~58 | 45~233 | 10~73 |

At the start of the administration, the hepatic function (SGOT/ASAT, SGPT/ALAT, LDH-L, alkaline phosphatase) of the tested dog was outside the normal range; however, as a result of the administration of the anticancer composition of the invention for 33 days to the dog, the data came to fall within the normal range, or got closer to the normal range. In addition, the creatine level was kept falling within the normal range throughout the test period, which confirmed the non-toxicity of the liquid preparation of Example 1. No cancer metastasis was found in the dog.

Test Example 3

Also in this Test Example, the liquid preparation obtained in Example 1 was tested for the anticancer effect thereof.

The liquid preparation prepared Example 1, having a concentration of 10%, was orally administered to an adult dog 12 (body weight, 23 kg±5 kg; 5 to 6 years old; mongrel with Dalmatian) having hemangiosarcoma, at a dose of 3 ml, twice a day continuously for 28 days; thereafter the same liquid preparation but having a concentration of 15% was administered thereto for 35 days and then the same liquid preparation but having a concentration of 20% was administered thereto for 9 days. Next, the same liquid preparation but having a concentration of 15% was administered to the dog for about 43 days, whereupon the dog was visually checked for the size of the tumor, and the tumor was obviously reduced. During the test, the body condition of the adult dog 12 was good, the appetite thereof was normal, and the body weight thereof did not significantly reduce. Like in Test Example 2, the dog was given a blood test during the test period. As a result, during the test period of 115 days, the adult dog 12 was not disordered and the liquid preparation of Example 1 was not toxic to the dog. In addition, there was no cancer metastasis in the dog. The liquid preparation having a concentration of 15% was kept administered to the dog further for 50 days, and the adult dog 12 did not change at all.

After this, the administration of the liquid preparation of Example 1 was stopped, and immediately the tumor of the adult dog 12 dramatically increased and the body weight thereof decreased by about 3 kg, and the dog weakened obviously.

Hemangiosarcoma is an extremely malignant cancer that is insidious and rapidly spreads by metastasis to produce sarcoma everywhere in the body; and the period from the tumor detection of hemangiosarcoma to the death is generally 6 to 8 weeks (42 to 56 days). Accordingly, the prompt weakening of the dog immediately after the stopping of the administration thereto of the liquid preparation of Example 1 could fall within the range of the prediction. Against such an extremely malignant cancer, the administration of the liquid preparation of Example 1 exhibited the effect thereof of reducing the tumor and inhibiting the tumor from enlarging for 165 days, and in addition, the tumor of the dog did not spread by metastasis and the body condition of the dog was kept good. These confirm the great usefulness of the liquid preparation of Example 1 as an anticancer composition especially for hemangiosarcoma.

It is known that the cure rate for hemangiosarcoma by surgical removal thereof is high. The results in Test Example 3 recommend a combination of medical therapy with the liquid preparation of Example 1 and surgical removal in clinical practice. This is because the administration of the liquid preparation of Example 1 was effective for preventing the tumor from enlarging and for preventing it from spreading by metastasis, and in addition, the body weight of the tested animal was kept as such and the body condition thereof was kept good, and there was found no problem in the blood test.

Test Example 4

Also in this Test Example, the liquid preparation obtained in Example 1 was tested for the anticancer effect thereof.

The liquid preparation prepared Example 1, having a concentration of 15%, was orally administered to an adult dog 13 (body weight, 25 kg±5 kg; 5 to 6 years old; mongrel) having sexually transmitted disease-infected tumor and malignant non-Hodgkin lymphoma, at a dose of 3 ml, three times a day continuously for 33 days. The circular glandular tumor having a size of about 12 cm at the start of the administration reduced to the size of 50%. In addition, the abdominal tumor also reduced to the size of 30% during the period.

Next, the same liquid preparation but having a concentration of 20% was administered to the dog for 34 hours, and the same preparation but having a concentration of 15% was thereto for 79 days. During the test period, the dog was given a blood test like in Test Example 2. As a result, only the LDH-L (lactate dehydrogenase-L) level slightly overstepped once above the normal range, but the others were all within the normal range. The temporary LDH-L level increase could be within the range of the error since the tumor size was still kept visually reducing even during the period. Accordingly, it has been confirmed that the long-term administration of the liquid preparation of Example 1 caused no change in the blood test data of the adult dog 13 and that the liquid preparation is effective for reducing the sexually transmitted disease-infected tumor and the malignant non-Hodgkin lymphoma of the tested dog.

Test Example 5

Also in this Test Example, the liquid preparation obtained in Example 1 was tested for the anticancer effect thereof.

An adult dog 14 (body weight, 30±5 kg; 6 to 7 years old; Maltese Herder) having mesenchymal tumor (soft tissue neoplasm) was first made to undergo a surgical operation to remove a part of the tumor; and after 6 days, the administration of the liquid preparation of Example 1 to the dug was started. This is because the tumor in the adult dog 14 suddenly increased. After the surgical removal operation and at the start of the liquid preparation administration, the adult dog 14 had symptoms of anemia as a result of the blood test thereof.

The liquid preparation of Example 1 having a concentration of 15% was orally administered to the dog, at a dose of 3 ml, three times a day continuously for 44 days. As a result, the tumor reduced to a size of 70%, and its dark color changed pink, and the dog changed for better in point of the clinical findings thereof. In addition, the dog recovered both in the appetite and in the body condition thereof.

During the test period, the dog was given a blood test like in Test Example 2. Of the blood test, the data of erythrocyte, hemoglobin and hematocrit are shown in Table 6 below.

TABLE 6

| | Adult dog 14 | | |
|---|---|---|---|
| | Erythrocyte ($10^6/\mu l$) | Hemoglobin (g/dl) | Hematocrit (%) |
| During the operation | 5 | 11.4 | 34 |
| After 30 days from dosing | 6.8 | 16.9 | 47 |
| Standard | 5.5~8.5 | 12~18 | 37~55 |

Table 6 confirms that, during the administration period of the liquid preparation of Example 1, the adult dog 14 that had had symptoms of anemia owing to the surgical operation for partial tumor removal recovered in point of all the data of erythrocyte, hemoglobin and hematocrit thereof, and that the adult dog 14 recovered from the sign of anemia. Accordingly, the results in Test Example 5 recommend a combination of medical therapy with the liquid preparation of Example 1 and surgical removal in clinical practice. This is because the administration of the liquid preparation of Example 1 to the anemic dog after surgical operation was effective for preventing the tumor still remaining after the removal operation from again enlarging and for further reducing the size of the remaining tumor, and in addition, the liquid preparation was effective for recovering the body condition of the dog from the sign of anemia. As the combination of the anticancer composition of the invention and surgical operation for removal, preferred is the combination thereof and surgical operation for partial removal, and more preferred is the combination thereof and surgical operation for partial removal of mesenchymal tumor (soft tissue neoplasm). This is because the tumor such as mesenchymal tumor (soft tissue neoplasm) that may frequently occur in a site in which the surgical operation for removal of the tumor is difficult may partly remain in the site still after the surgical operation for removal thereof, and in such a case, it may be possible to substantially recover the dog from cancer by the use of the anticancer composition of the invention.

Test Example 6

In this Test Example, the composition of the liquid preparation obtained in Example 1 was analyzed. The result is shown in Table 7 below. In Table 7, "% RDA" means the food safety regulation level (recommended daily allowance) for humans.

TABLE 7

| Atom | Amount | % RDA |
|---|---|---|
| P (mg/100 mg) | 12.92 | 350 |
| Ca (mg/100 ml) | 11.36 | 800~1200 |
| Ba (mg/L) | <0.4 | 7.3 |
| As (ppm) | 0.008 | 7~12 |
| Se (μg/L) | <20 | 45~70 |
| Hg (μg/L) | <20 | 144 |
| Na (mg/100 ml) | 40.68 | 90~100 |
| K (mg/100 ml) | 210.94 | 1000~3500 |

TABLE 7-continued

| Atom | Amount | % RDA |
|---|---|---|
| Pb (ppm) | 0.12 | 5 |
| Cu (mg/100 ml) | 0.06 | 1.5~3 |
| Fe (mg/100 ml) | 1.32 | 10~15 |
| Mg (mg/100 ml) | 0.25 | 350 |
| Mn (mg/100 ml) | 0.082 | 2~9 |
| Zn (mg/100 ml) | 0.23 | 12~15 |

Table 7, indicating the analytical data of the composition thereof, confirms that the liquid preparation obtained in Example 1 has no negative influence on human bodies.

As in the above, the anticancer composition of Example 1 bettered the systemic condition of the adult dogs. In addition, the anticancer compositions of Example 1 has no side-effects to cause general sick feeling such as vomiting, diarrhea and the like, and has no side-effects on immunity; and during the cancer treatment test period, the adult dogs bettered in point of the appetite increase and the body weight increase thereof. Further, in oral administration of the preparations within the concentration range in Examples, the blood test data did not significantly overstep the normal range, and the kidney function and the liver function of the tested dogs were kept good. Regarding the anticancer effect thereof, in particular, the anticancer composition was especially excellent in the effect of promptly suppressing and reducing tumor and in the effect of prolonging the survival period by maintaining the effect thereof of long-term cancer suppression and reduction. On the other hand, it has been confirmed that the anticancer composition of the invention has no negative influence on human bodies.

The invention claimed is:

1. A method for treating cancer, comprising administering to a subject suffering from cancer an effective amount of a composition comprising a flowery portion of elm tree or its extract and a leaf portion of varnish tree or its extract, wherein the cancer is selected from the group consisting of malignant sarcoma, malignant adenoma, hemangiosarcoma, non-Hodgkin lymphoma, mesenchymal tumor and soft tissue sarcoma wherein the composition comprising a 10% concentration of a 70% ethanol extract of a mixture of 7.5 g dry powder from the flowery portion of elm tree and 7.5 g dry powder from the leaf portion of varnish tree concentrated to a solid content of 58% by weight.

2. The method of claim 1, wherein the cancer is malignant sarcoma.

3. The method of claim 1, wherein the cancer is malignant adenoma.

4. The method of claim 1, wherein the cancer is hemangiosarcoma.

5. The method of claim 1, wherein the cancer is non-Hodgkin lymphoma.

6. The method of claim 1, wherein the cancer is mesenchymal tumor.

7. The method of claim 1, wherein the cancer is soft tissue sarcoma.

8. The method of claim 2, wherein the subject suffering from a malignant sarcoma is treated by surgical removal of the malignant sarcoma together with administration of a composition comprising a 10% concentration of a 70% ethanol extract of a mixture of 7.5 g dry powder from the flowery portion of elm tree and 7.5 g dry powder from the leaf portion of varnish tree concentrated to a solid content of 58% by weight.

* * * * *